US010099070B2

(12) United States Patent
Mougenot

(10) Patent No.: US 10,099,070 B2
(45) Date of Patent: Oct. 16, 2018

(54) MEDICAL APPARATUS FOR RADIOTHERAPY AND ULTRASOUND HEATING

(71) Applicant: KONINKLIJKE PHILIPS N.V., Eindhoven (NL)

(72) Inventor: Charles Mougenot, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 347 days.

(21) Appl. No.: 15/033,947

(22) PCT Filed: Nov. 7, 2014

(86) PCT No.: PCT/EP2014/074107
§ 371 (c)(1),
(2) Date: May 3, 2016

(87) PCT Pub. No.: WO2015/067786
PCT Pub. Date: May 14, 2015

(65) Prior Publication Data
US 2016/0263404 A1    Sep. 15, 2016

(30) Foreign Application Priority Data

Nov. 8, 2013   (EP) .................................... 13192082

(51) Int. Cl.
*A61N 7/02*       (2006.01)
*A61B 5/055*      (2006.01)
(Continued)

(52) U.S. Cl.
CPC ................ *A61N 7/02* (2013.01); *A61B 5/055* (2013.01); *A61B 34/10* (2016.02); *A61N 5/1039* (2013.01);
(Continued)

(58) Field of Classification Search
CPC .......... A61N 2005/1087; A61N 5/1039; A61N 5/1064; A61N 5/1067; A61N 5/1081; A61N 7/02
See application file for complete search history.

(56) References Cited

U.S. PATENT DOCUMENTS

2010/0185080 A1    7/2010  Gunnar

FOREIGN PATENT DOCUMENTS

DE       102007060189 A1    2/2009

OTHER PUBLICATIONS

Neo-adjuvant chemotherapy alone or with regional hyperthermia for localised high-risk soft-tissue sarcoma: a randomised phase 3 multicentre study. Issels RD, Lindner LH, Verweij J, Wust P, Reichardt P, Schem BC, Abdel-Rahman S, Daugaard S, Salat C, Wendtner CM, Vujaskovic Z, Wessalowski R, Jauch KW, Dürr HR, Ploner F, Baur-Melnyk A, Mansmann U, Hiddemann W, Blay JY, Hohenberger P; European Society for Hyperthermic Oncology (ESHO). Lancet Oncol. Jun. 2010; 11(6):561-70.
(Continued)

*Primary Examiner* — Christine H Matthews

(57) ABSTRACT

The invention provides for a medical apparatus comprising a processor. Execution instructions causes the processor to receive a treatment plan descriptive of an ionizing radiation beam treatment of a target zone within a subject using a radiation beam therapy system with a radiation source and a gantry. The radiation source is operable for aiming a radiation beam path at a rotational axis of the gantry. The instructions further cause the processor to receive a planning thermal distribution descriptive of ultrasound heating of the subject with a high intensity focused ultrasound system of a heating zone and an ultrasound beam path within the subject. The target zone is within the heating zone. The instructions further cause the processor to generate radiation control
(Continued)

command data using the planning thermal distribution and the treatment plan. The radiation control command data is executable to cause the radiation source to reduce irradiation of the target zone when more than a predetermined volume of the radiation beam path intersects the ultrasound beam path.

15 Claims, 13 Drawing Sheets

(51) Int. Cl.
    *A61N 5/10*     (2006.01)
    *G01R 33/48*     (2006.01)
    *A61B 17/00*     (2006.01)
    *A61B 34/10*     (2016.01)
    *A61B 90/00*     (2016.01)

(52) U.S. Cl.
    CPC ......... *A61N 5/1067* (2013.01); *A61N 5/1081* (2013.01); *G01R 33/4814* (2013.01); *A61B 2017/00084* (2013.01); *A61B 2034/101* (2016.02); *A61B 2034/105* (2016.02); *A61B 2090/374* (2016.02); *A61N 5/1064* (2013.01); *A61N 2005/1087* (2013.01); *G01R 33/4804* (2013.01)

(56) References Cited

OTHER PUBLICATIONS

Eduardo G. Moros, Jose Peñagaricano, Peter Novà K, William L Straube and Robert J. Myerson. "Present and future technology for simultaneous superficial thermoradiotherapy of breast cancer". Int. J. Hyperthermia, Oct. 2010; 26(7): 699-709.

Cervical cancer: radiotherapy and hyperthermia. van der Zee J, van Rhoon GC. Int J Hyperthermia. May 2006; 22(3):229-34.

Modelling heat-induced radiosensitization: clinical implications. Myerson RJ, Roti Roti JL, Moros EG, Straube WL, Xu M. Int J Hyperthermia. Mar. 2004; 20(2):201-12.

Sapareto et al "Thermal Dose Determination in Cancer Therapy" International Journal of Radiation Oncology Biology Physics, vol. 10, Issue 6, p. 787-800, Apr. 1984.

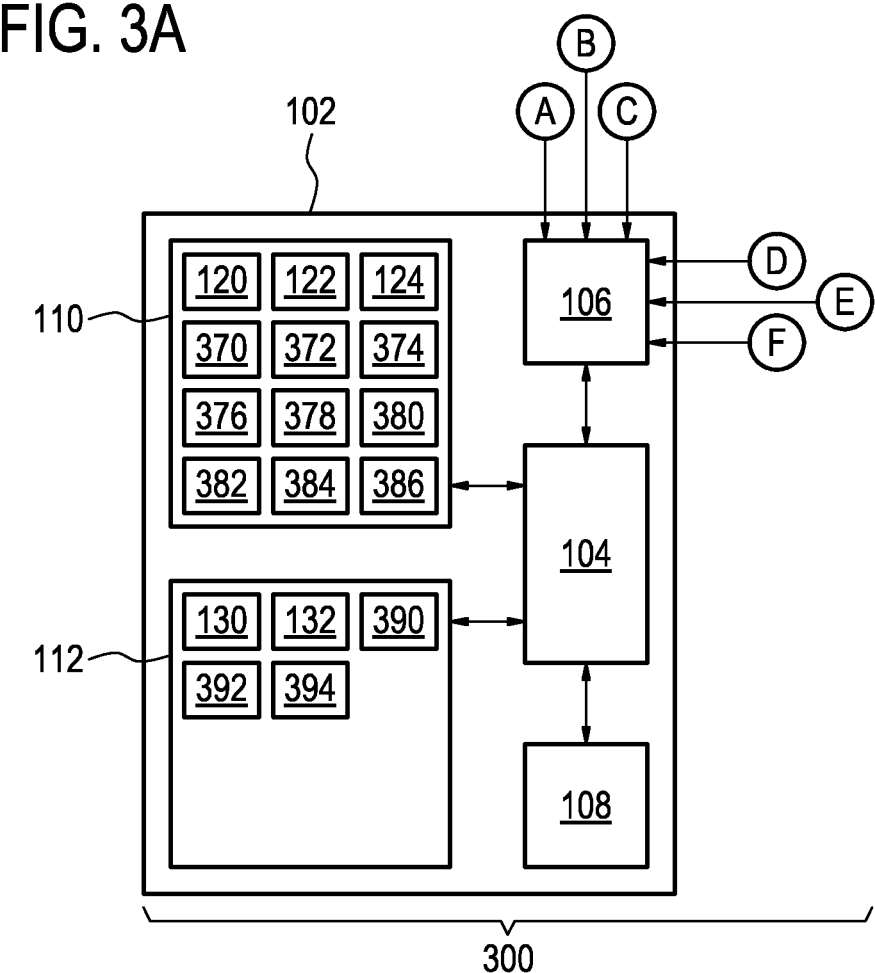

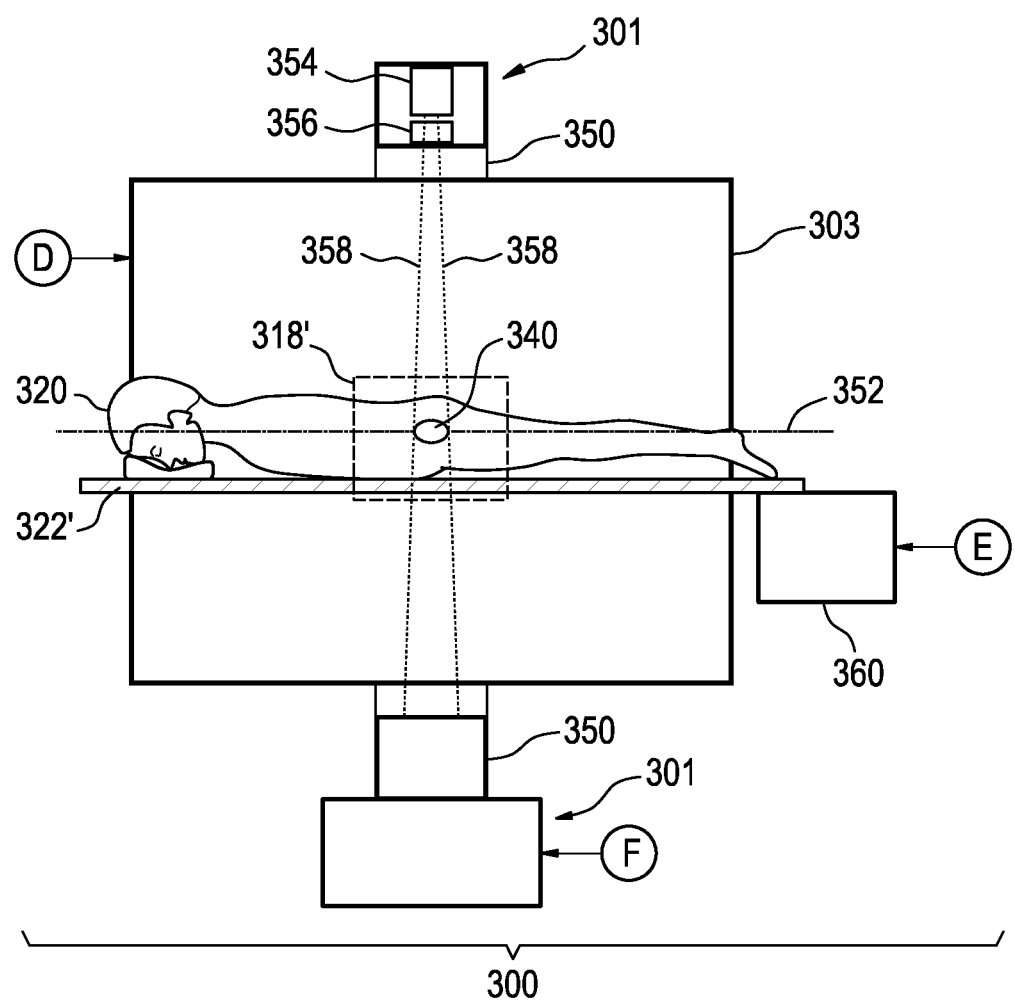

MEDICAL APPARATUS FOR RADIOTHERAPY AND ULTRASOUND HEATING

CROSS REFERENCE TO RELATED APPLICATIONS

This application is a U.S. national phase application of International Application No. PCT/EP2014/074107, filed on Nov. 7, 2014, which claims the benefit of EP Application Serial No. 13192082.9 filed on Nov. 8, 2013 and is incorporated herein by reference.

TECHNICAL FIELD

The invention relates to radiation beam therapy, in particular to radiation beam therapy combined with hyperthermia.

BACKGROUND OF THE INVENTION

Mild hyperthermia (HT) is a therapeutic technique in which tissue is heated to temperatures (e.g., 38-45° C.) above body temperature, but below ablative temperatures. These hyperthermia treatments may result in physiological (e.g., perfusion) and cellular (e.g., gene expression) changes that improve the therapeutic effectiveness when used in conjunction with chemotherapy or radiation therapy. HT induces a multitude of changes, which provide clinical benefits that make it synergistic with many chemotherapeutic agents and radiation therapy. In addition to physiological and cellular changes, hyperthermia may be used with temperature responsive or non-responsive drug delivery systems to reduce toxicity and improve overall efficacy.

There are a number of currently available devices that can heat target tissue to the hyperthermic range. One example is radiofrequency (RF) applicators, which use tuned antennas to transmit RF energy into the body. However, RF applicators are best used to heat deep-seated tumors, due the long wavelengths of RF. Microwave applicators are also used, but are typically used only for superficial tumors due to their small wavelength. Both types can be used in different configurations, with the most common being phased arrays, waveguides, and spiral antennas. An efficient way of performing local hyperthermia is by magnetic resonance guided high intensity focused ultrasound (MR-HIFU), in which focused ultrasound is used for achieving hyperthermia and MR is utilized to monitor the treatment.

The journal article Moros et. al., "Present and future technology for simultaneous superficial thermoradiotherapy of breast cancer," Int. J. Hyperthermia, October 2010; 26(7) 699-709 discloses an apparatus for simultaneous thermoradiotherapy. Radiation is applied using a dual-frequency SURLAS applicator where radiation and ultrasound are applied in the same direction: the radiation necessarily travels through the near field region of the ultrasound. The German patent application DE 10 2007 060 189 mentions a system for radiation therapy which includes irradiation by way of both a radiation therapy beam as well as with high-intensity focused ultrasound (HIFU). The German patent application DE 10 2007 060 189 points to synergetic effects that occur when simultaneously radiation therapy and hyperthermia are applied.

SUMMARY OF THE INVENTION

In one aspect the invention provides a medical apparatus, a computer program product, and a method in the independent claims. Embodiments are given in the dependent claims.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Medical image data is defined herein as two or three dimensional data that has been acquired using a medical imaging scanner. A medical imaging scanner is defined herein as a apparatus adapted for acquiring information about the physical structure of a patient and construct sets of two dimensional or three dimensional medical image data. Medical image data can be used to construct visualizations or a medical image which are useful for diagnosis by a physician. This visualization can be performed using a computer. Medical image data as used herein may also encompasses data which is descriptive of anatomical structures of a subject.

Magnetic Resonance (MR) data is defined herein as being the recorded measurements of radio frequency signals emitted by atomic spins by the antenna of a Magnetic resonance apparatus during a magnetic resonance imaging scan. Magnetic resonance data is an example of medical image data. A Magnetic Resonance Imaging (MRI) image is defined herein as being the reconstructed two or three dimensional visualization of anatomic data contained within the magnetic resonance imaging data. This visualization can be performed using a computer. A magnetic resonance image is a type of medical image.

MR thermometry data is defined herein as being the recorded measurements of radio frequency signals emitted by atomic spins by the antenna of a Magnetic resonance apparatus during a magnetic resonance imaging scan which contains information which may be used for magnetic resonance thermometry. Magnetic resonance thermometry functions by measuring changes in temperature sensitive parameters. Examples of parameters that may be measured during magnetic resonance thermometry are: the proton resonance frequency shift, the diffusion coefficient, or changes in the T1 and/or T2 relaxation time may be used to measure the temperature using magnetic resonance. The proton resonance frequency shift is temperature dependent, because the magnetic field that individual protons, hydrogen atoms, experience depends upon the surrounding molecular structure. An increase in temperature decreases molecular screening due to the temperature affecting the hydrogen bonds. This leads to a temperature dependence of the proton resonant frequency. The proton density depends linearly on the equilibrium magnetization. It is therefore possible to determine temperature changes using proton density weighted images.

The relaxation times T1, T2, and T2-star (sometimes written as T2*) are also temperature dependent. The reconstruction of T1, T2, and T2-star weighted images can therefore be used to construct thermal or temperature maps.

The temperature also affects the Brownian motion of molecules in an aqueous solution. Therefore pulse sequences which are able to measure diffusion coefficients such as a pulsed diffusion gradient spin echo may be used to measure temperature.

One of the most useful methods of measuring temperature using magnetic resonance is by measuring the proton resonance frequency (PRF) shift of water protons. The resonant frequency of the protons is temperature dependent. As the temperature changes in a voxel the frequency shift will cause the measured phase of the water protons to change. The temperature change between two phase images can therefore be determined. This method of determining temperature has the advantage that it is relatively fast in comparison to the other methods. The PRF method is discussed in greater detail than other methods herein. However, the methods and techniques discussed herein are also applicable to the other methods of performing thermometry with magnetic resonance imaging.

An 'ultrasound window' as used herein encompasses a window which is able to transmit ultrasonic waves or energy. Typically a thin film or membrane is used as an ultrasound window. The ultrasound window may for example be made of a thin membrane of BoPET (Biaxially-oriented polyethylene terephthalate).

In one aspect the invention provides for a medical apparatus comprising a memory containing machine-executable instructions for execution by a processor. The medical apparatus further comprises a processor for controlling the medical apparatus. Execution of the machine-executable instructions cause the processor to receive a treatment plan prescriptive of an ionizing radiation beam treatment of a target zone within a subject using a radiation beam therapy system. The radiation beam therapy system comprises a radiation source and a gantry for rotating the radiation source about a rotational axis. The radiation source is operable for irradiating a radiation beam path.

The radiation source is operable for aiming the radiation beam path at the rotational axis. Execution of the machine-executable instructions further cause the processor to receive a planning thermal distribution descriptive of ultrasound heating of the subject with a high-intensity focused ultrasound system. The planning thermal distribution is spatially dependent. The planning thermal distribution is descriptive of a heating zone and an ultrasound beam path within the subject. The target zone is within the heating zone. In some examples the planning thermal distribution is measured. In other examples the planning thermal distribution is calculated using a model.

Execution of the machine-executable instructions further cause the processor to generate radiation control command data for controlling the radiation beam therapy system to irradiate the target zone using the planning thermal distribution and the treatment plan. The radiation control command data is executable to cause the radiation source to reduce irradiation of the target zone when more than a predetermined volume of the radiation beam path intersects the ultrasound beam path. This embodiment may be beneficial because the radiation beam is used to irradiate the target zone only when the radiation beam does not overlap the ultrasound beam path more than a certain amount. This may have the effect of reducing the effect of radiation on portions of the subject outside of the target zone.

The ultrasound beam path as used herein may encompass the near field region and/or possibly the far field region of the ultrasound beam. The ultrasound beam path is a region outside of the heating zone, where the thermal distribution is above a predetermined threshold.

The planning thermal distribution may be defined in a number of ways. For instance the planning thermal distribution could be defined in terms of a thermal dose. In another example the planning thermal distribution could be for instance the interval in time when part of the subject is above a certain temperature.

The treatment plan may be descriptive of more than just an ionizing radiation beam treatment of a target zone. The treatment plan may for instance specify portions of the subject's anatomy which may be used as a landmark for registering medical image data such as CT images or magnetic resonance images to the treatment plan. The treatment plan may also contain data on a desired thermal dose or thermal distribution within the subject. The treatment plan may also describe the position or location of the tumor or target zone and also possibly the locations of organs with a specified radiation dose and average temperature or thermal dose for those regions.

In another embodiment execution of the instructions further cause the processor to calculate the predicted thermal distribution and ultrasound control command data using the treatment plan and a high-intensity focused ultrasound simulation model. The ultrasound control command data is executable for controlling a high-intensity focused ultrasound system to cause the high-intensity focused ultrasound system to heat the subject according to the predicted thermal distribution. The high-intensity focused ultrasound simulation model is descriptive of the high-intensity focused ultrasound system. This embodiment may be beneficial because a model of how the high-intensity focused ultrasound system can be used to sonicate the subject is used to both determine the planning thermal distribution and also commands which may be used to control the high-intensity focused ultrasound system.

The planning thermal distribution is used in the process of generating or planning the radiation control command data because typically there is less flexibility in the ultrasound sonication of a subject in comparison to controlling the ionizing radiation beam for irradiating the subject. This is because the ultrasound may only enter the subject at certain points and needs to travel to the target zone. For instance the ribs or bones or other tissue such as the lungs may restrict the directions and positions which ultrasound can be used to sonicate the subject.

In another embodiment the planning thermal distribution is the predicted thermal distribution. Execution further cause the processor to first control the radiation beam therapy system to execute the radiation therapy control commands and to second control the high-intensity focused ultrasound system to execute the ultrasound control command data. In this embodiment the subject is first irradiated and then the subject is sonicated. As the irradiation takes place first the predicted thermal distribution which was calculated using the high-intensity focused ultrasound simulation model should be used when planning generating the radiation control command data. In this embodiment it may also be possible to estimate the actual radiation dose to the subject and use this to later modify the ultrasound control command data.

In another embodiment execution of the instructions further causes the processor to control the radiation beam therapy system to execute the radiation therapy control commands and control the high-intensity focused ultrasound system to execute the ultrasound control command data simultaneously. In this embodiment the predicted thermal distribution is calculated using the high-intensity focused ultrasound simulation model and then the irradiation of the subject and the heating of the subject using the high-intensity focused ultrasound system are performed at the same time. If they are performed simultaneously it means that at least a portion of the commands used for controlling the radiation beam therapy system and the commands for controlling the high-intensity focused ultrasound system are performed such as they overlap in time.

In another embodiment execution of the instructions further cause the processor to acquire thermal magnetic resonance data which is descriptive of the heating zone and the ultrasound beam path using the magnetic resonance imaging system during execution of the ultrasound control command data. Execution of the instructions further causes the processor to calculate a measured thermal distribution using the thermal magnetic resonance data. Execution of the instructions further cause the processor to modify the radiation control command data using the treatment plan and the measured thermal distribution. In this embodiment the heating and irradiation of the subject takes place simultaneously or at least partially overlapping and the thermal magnetic resonance data is used to compensate for heating as it takes place. If the heating of the subject is not exactly as was determined by the predicted thermal distribution then the radiation control command data can be modified on the fly to account for this change.

In another embodiment the planning thermal distribution is a measured thermal distribution. Execution of the instructions further cause the processor to first control the high-intensity focused ultrasound system to execute the ultrasound control command data and second control the radiation beam therapy system to execute the radiation therapy control commands. Execution of the instructions further cause the processor to acquire thermal magnetic resonance data descriptive of the heating zone and the ultrasound beam path using the magnetic resonance imaging system during the execution of the ultrasound control command data. Execution of the instructions further causes the processor to calculate the measured thermal distribution using the thermal magnetic resonance data. In this embodiment the subject is first heated with the high-intensity focused ultrasound system and a measured thermal distribution is measured using a magnetic resonance imaging system. Next this measured thermal distribution is used as the planning thermal distribution and radiation control command data are generated.

In another embodiment the medical apparatus further comprises the high-intensity focused ultrasound system.

In another embodiment the medical apparatus further comprises the high-intensity focused ultrasound system and the high-intensity focused ultrasound system is incorporated into a magnetic resonance imaging system.

In another embodiment the medical apparatus further comprises the radiation therapy system. It is possible that the radiation therapy system may also incorporate or comprise a medical imaging system for example a magnetic resonance imaging system or a computer tomography system.

In another embodiment the medical apparatus further comprises the radiation therapy system. The radiation therapy system further comprises the high-intensity focused ultrasound system. The radiation therapy system further comprises a magnetic resonance imaging system. If a magnetic resonance imaging system is used then the magnetic resonance imaging system could be used for several different purposes such as measuring the thermal magnetic resonance data and also for registering the treatment plan to the high-intensity focused ultrasound system and/or radiation therapy system.

In another embodiment the radiation beam therapy system is a LINAC system.

In another embodiment the radiation beam therapy system is a charged radio therapy system.

In another embodiment the radiation beam therapy system is an X-ray system.

In another embodiment the radiation beam therapy system is a gamma radiation therapy system such as a gamma knife.

In another embodiment the planning thermal distribution is descriptive of a local average temperature divided by time. For example the temperature during hyperthermia induced by the high-intensity focused ultrasound system may be kept below the following temperatures in the target zone: below 45° C., below 44° C., below 43° C., below 42° C., below 41° C., or below 40° C.

In another embodiment the planning thermal distribution is a thermal dose. The thermal dose may for instance be defined in the manner described in Sapareto and Dewey, "Thermal dose determination in cancer therapy," International Journal of Radiation Oncology* Biology* Physics, Volume 10, Issue 6, Pages 787-800, April 1984, doi: 10.1016/0360-3016(84)90379-1. Other definitions of the thermal dose may also be used.

In another aspect the invention provides for a computer program product comprising machine-executable instructions for execution by a processor controlling the medical apparatus. The medical apparatus comprises the processor. Execution of the machine-executable instructions cause the processor to receive a treatment plan descriptive of an ionizing radiation beam treatment of a target zone within a subject using a radiation beam therapy system. The radiation beam therapy system comprises a radiation source and a gantry for rotating the radiation source about a rotational axis. The radiation source is operable for irradiating the radiation beam path. The radiation source is operable for aiming the radiation beam path at the rotational axis. Execution of the machine-executable instructions further cause the processor to receive a planning thermal distribution descriptive of ultrasound heating of the subject with a high-intensity focused ultrasound system. The planning thermal distribution is spatially dependent. The planning thermal distribution is descriptive of a heating zone and an ultrasound beam path within the subject. The target zone is within the heating zone. Execution of the instructions further cause the processor to generate radiation control command data for controlling the radiation beam therapy system to irradiate the target zone using the planning thermal distribution and the treatment plan. The radiation control command data is executable to cause the radiation source to reduce irradiation of the target zone when more than a predetermined volume of the radiation beam intersects the ultrasound beam path.

In another example the invention provides for a method of operating a medical apparatus. The method comprises the step of receiving a treatment plan descriptive of an ionizing radiation beam treatment of a target zone within a subject using a radiation beam therapy system. The radiation beam therapy system comprises a radiation source and a gantry for rotating the radiation source about a rotational axis. The radiation source is operable for irradiating a radiation beam path. The radiation source is operable for aiming the radiation beam path at the rotational axis. The method further comprises the step of receiving a planning thermal distribution descriptive of ultrasound heating of the subject with a high-intensity focused ultrasound system. The planning thermal distribution is spatially dependent. The planning thermal distribution is descriptive of a heating zone and an ultrasound beam path within the subject. The target zone is within the heating zone. The method further comprises the step of generating radiation control command data for controlling the radiation beam therapy system to irradiate the target zone using the planning thermal distribution and the treatment plan. The radiation control command data is executable to cause the radiation source to reduce irradiation of the target zone when more than a predetermined volume of the radiation beam path intersects the ultrasound beam path.

In another aspect the invention provides for a method of radiation therapy comprising the step of receiving a treatment plan. The treatment plan is descriptive of an ionizing radiation beam treatment of a target zone within a subject using a radiation beam therapy system. The radiation beam therapy system comprises a radiation source and a gantry for rotating the radiation source about the rotational axis. The radiation source is operable for irradiating a radiation beam path. The radiation source is operable for aiming the radiation beam path at the rotational axis. The method further comprises the step of placing a subject into a high-intensity focused ultrasound system. The high-intensity focused ultrasound system comprises a magnetic resonance imaging system. The method further comprises the step of acquiring planning magnetic resonance data using the magnetic resonance imaging system. The method further comprises the step of generating ultrasound control command data for controlling the high-intensity focused ultrasound system using a high-intensity focused ultrasound simulation model, the treatment plan, and the planning magnetic resonance data. The high-intensity focused ultrasound simulation model is descriptive of the high-intensity focused ultrasound system.

The method further comprises the step of sonicating the subject by executing the ultrasound control command data. The method further comprises the step of measuring thermal magnetic resonance data during the sonication of the subject. The method further comprises the step of calculating a measured thermal distribution using the thermal magnetic resonance data. The method further comprises the step of placing a subject into the radiation therapy beam system. The radiation beam therapy system comprises a medical imaging system for acquiring medical image data. The method further comprises the step of generating ionizing radiation control command data for controlling the radiation beam therapy system to irradiate the target zone using the measured thermal distribution, the treatment plan, and the medical image data. The radiation control command data is executable to cause a radiation source to reduce irradiation of target zone when more than a predetermined volume of the radiation beam path intersects the ultrasound beam path. The method further comprises the step of irradiating the subject by executing the radiation control command data.

In the above example of the radiation therapy method, there may be variations. For example in the above the subject was sonicated before being irradiated. In other examples the subject may be irradiated first and then sonicated. In yet another example the sonication and the irradiation of the subject may be performed such that they are at least partially overlapping.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
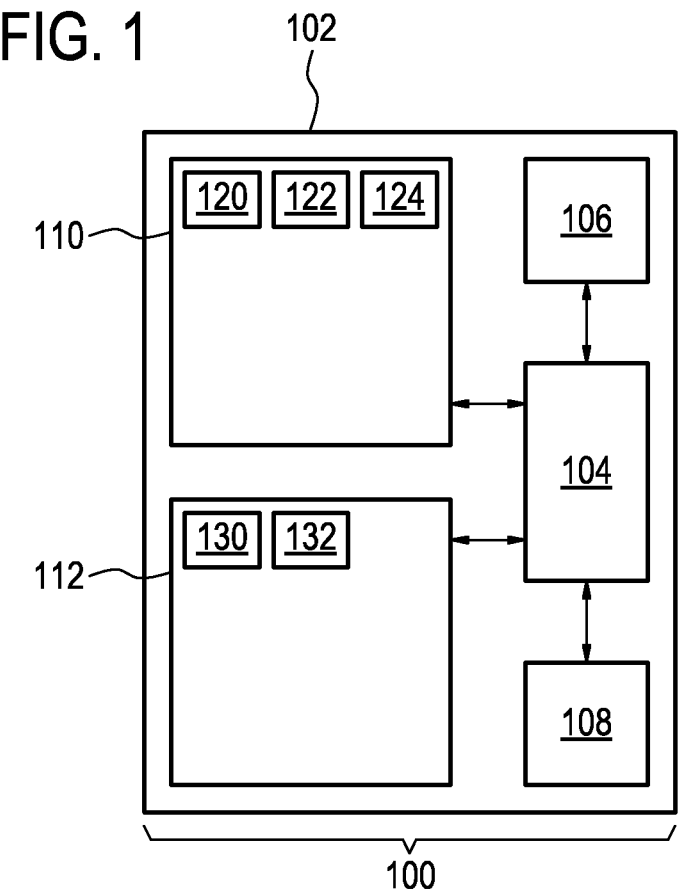
FIG. 1 illustrates an example of a medical apparatus.

FIG. 1 shows an example of a medical apparatus 100. The medical apparatus is shown as comprising a computer 102. The computer 102 has a processor 104. The processor 104 is connected to a hardware interface 106. The hardware interface may enable the processor 104 to control other components of the medical apparatus 100. For example in other examples the medical apparatus 100 may comprise other components such as a high-intensity focused ultrasound system or even a radiation therapy system. The processor 104 is shown as being connected also to an optional user interface 108. The processor 104 is also in communication or connected to computer storage 110 and computer memory 112. The contents of the computer storage 110 and the computer memory 112 may be interchangeable or items within the storage 110 and the memory 112 may be duplicated. This is true for the example shown in FIG. 1 and also in later examples.

The computer storage 110 is shown as containing a treatment plan 120 that has been received for example via the user interface 108 or possibly also via a computer connection or network connection. The computer storage 110 is further shown as containing planning thermal distribution 122 which has also been the received via the user interface 108, a network connection, or may possibly have been received by further calculations or processing by the processor 104. The computer storage 110 is further shown as containing radiation control command data 124.

The computer memory 112 is shown as containing a control module 130. The control module contains code which enables the processor 104 to control the operation and function of the medical apparatus 100. In some examples the control module 130 may enable the processor 104 to control other additional components of the apparatus via the hardware interface 106. For instance it may enable the processor 104 to send and receive commands to control a high-intensity focused ultrasound system, a medical imaging system, and/or a radiation beam therapy system. The computer memory 112 is shown as further containing a radiation control command generation module 132 that contains code which enables the processor 104 to generate the radiation control command data 124 using the treatment plan 120 and the planning thermal distribution 122.

Figure 2:
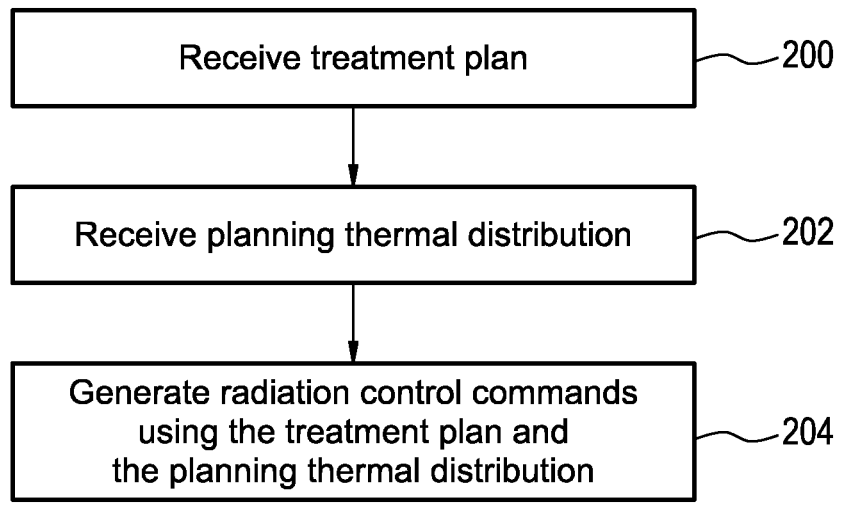
FIG. 2 shows a flow chart which illustrates a method of operating the medical apparatus of FIG. 1.

FIG. 2 shows a flowchart which illustrates a method of controlling the medical apparatus 100 shown in FIG. 1. First in step 200 a treatment plan 120 descriptive of an ionizing radiation beam treatment of a target zone within the subject using a radiation beam therapy system is received. The radiation therapy system comprises a radiation source and a gantry for rotating the radiation source around a rotational axis. The radiation source is operable for irradiating a radiation beam path. The radiation source is operable for aiming the radiation beam path at the rotational axis. Next in step 202 a planning thermal distribution 122 is received. The planning thermal distribution 202 is descriptive of ultrasound heating of the subject with a high-intensity focused ultrasound system. The planning thermal distribution is spatially dependent. The planning thermal distribution is descriptive of a heating zone and an ultrasound beam path within the subject. The target zone is within the heating zone.

Next in step 204 radiation control command data are generated. The radiation control command data are for controlling the radiation beam therapy system to irradiate the target zone using the planning thermal distribution 122 and the treatment plan 120. The radiation control command data 124 are operable to cause the radiation source to reduce irradiation of the target zone when more than a predetermined volume of the radiation beam path intersects the ultrasound beam path.

Figure 3B:
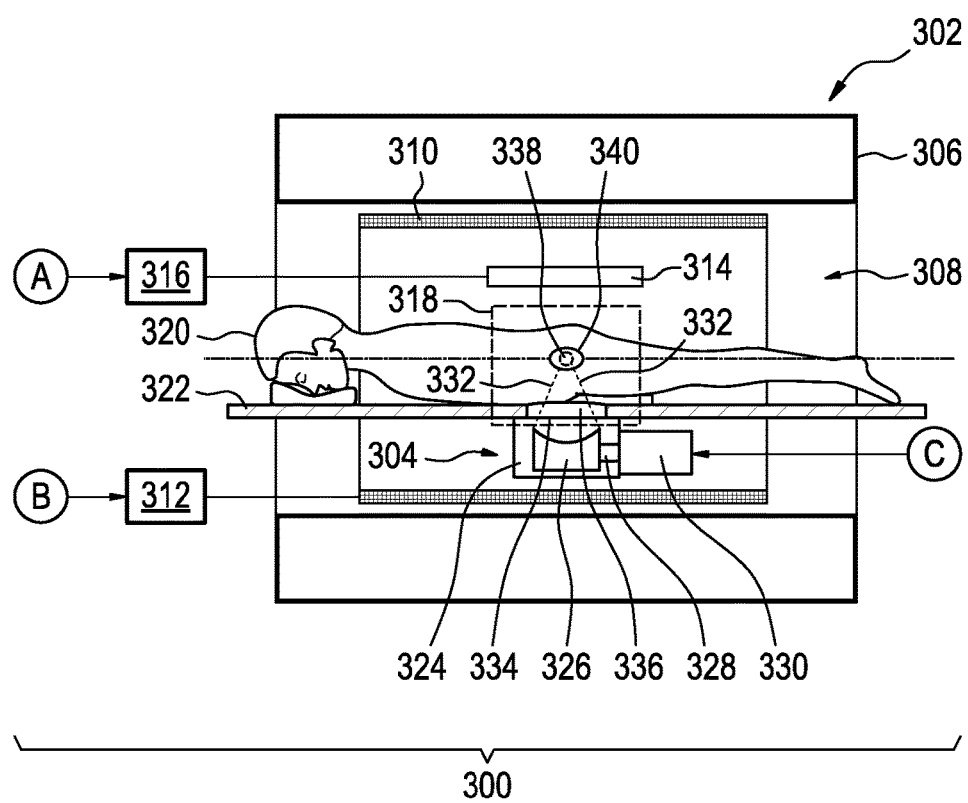
FIG. 3 illustrates a further example of a medical apparatus.

FIGS. 3a, 3b and 3c illustrate an example of a medical apparatus 300. In these figures a letter within a circle indicates connections between different portions of the figures.

The medical apparatus 300 comprises a computer 102 as was illustrated in FIG. 1. In addition the medical apparatus 300 comprises a radiation beam therapy system 301 that is integrated with a medical imaging system 303. The medical apparatus 300 also comprises a magnetic resonance imaging system 302 integrated with a high-intensity focused ultrasound system 304.

The magnetic resonance imaging 302 system comprises a magnet 306. The magnet shown in FIG. 3B is a cylindrical type superconducting magnet. The magnet has a liquid helium cooled cryostat with superconducting coils. It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 308 of the cylindrical magnet 306 there is an imaging zone 318 where the magnetic field is strong and uniform enough to perform magnetic resonance imaging.

Within the bore 306 of the magnet there is also a magnetic field gradient coil 310 which is used to spatially encode magnetic spins within an imaging zone of the magnet during the acquisition of magnetic resonance data. The magnetic field gradient coil 310 is connected to a magnetic field gradient coil power supply 312. The magnetic field gradient coil is intended to be representative. Typically magnetic field gradient coils contain three separate sets of coils for spatially encoding in three orthogonal spatial directions. A magnetic field gradient power supply supplies current to the magnetic field gradient coils. The current supplied to the magnetic field coils is controlled as a function of time and may be ramped or pulsed.

In the center of the bore 308 is an imaging zone 318. Adjacent to the imaging zone is a radio-frequency coil 314 which is connected to transceiver 316. Also within the bore 308 is a subject 320 reposing on a subject support 322. The radio-frequency coil 314 is adapted for manipulating the orientations of magnetic spins within the imaging zone and for receiving radio transmissions from spins also within the imaging zone. The radio-frequency coil 314 may contain multiple coil elements. The radio-frequency coil may also be referred to as a channel or an antenna. The radio-frequency coil 314 and radio frequency transceiver 316 may be replaced by separate transmit and receive coils and a separate transmitter and receiver. It is understood that the radio-frequency coil 314 and the radio frequency transceiver 316 are representative. The radio-frequency coil 314 is intended to also represent a dedicated transmit antenna and a dedicated receive antenna. Likewise the transceiver may also represent a separate transmitter and receivers.

The high-intensity focused ultrasound system 304 comprises a fluid-filled chamber 324 which houses an ultrasound transducer 326. The ultrasound transducer 326 is mechanically positioned by a mechanical positioning system 328. There is an actuator 330 for actuating the mechanical positioning system. In alternative embodiments the ultrasound transducer may be a manually positioned external transducer without the fluid-filled chamber 324 or mechanical positioning system 328.

The ultrasonic transducer 326 may also contain multiple elements for emitting ultrasound. A power supply which is not shown may control the amplitude and/or phase and/or frequency of alternating current electric power supplied to the elements of the ultrasonic transducer 326. The dashed lines 332 show the path of ultrasound from the ultrasonic transducer 326. The ultrasound 332 first passes through the fluid-filled chamber 324. The ultrasound then passes through an ultrasound window 334. After passing through the ultrasound window 334 the ultrasound passes through an optional gel pad 336 which may be used to conduct ultrasound between the window 334 and the subject 320. The ultrasound 332 then enters the subject 320 and is focused into a focal or sonication point 338. There is a region 340 which is a target zone. Through a combination of electronic and mechanical positioning of the sonication point 338 the entire target zone 340 can be heated through a combination of heating and maintaining trajectories. The target zone 340 is within the imaging zone 318.

The medical imaging system 303 has an imaging zone 318' for acquiring medical image data from a subject 320. The radiation beam therapy system 301 comprises a gantry 350 which is mounted about the medical imaging system 303. An axis of rotation 352 of the gantry 350 is shown as going directly through the target zone 340. The subject 320 is on a subject support 322'. A support positioning system 360 may for instance be used to position the subject support 322' to move the target zone 340 into the axis 352.

The radiation beam therapy system 301 has a radiation source 352 and a collimator 356 positioned such that they are aimed at the axis 352. The gantry 350 is able to rotate the radiation source 354 and the optional collimator 356. This enables the radiation source 354 to spin about the subject 320 and irradiate the target zone 340 from different angles. The path of the radiation beam 358 is shown in dashed lines and can be seen as intersecting the target zone 340.

The gantry 350 which is used to rotate a radiation source 354 about the magnet 306. The gantry 350 rotates about the axis of rotation 352. There is a radiation source 354 which is rotated by the gantry 350. The radiation source 354 generates a radiation beam 358 which passes through a collimator 356. In the Fig. the target zone is labeled 340. It can be noticed that the target zone 354 is located on the axis of rotation 352. As the radiation source 354 rotates about the axis of rotation 354 the target zone 340 is always targeted. There is also a support positioning system 360 for positioning the support 322' to position the location of the target zone 340 relative to the subject 320.

The magnetic field gradient coil power supply 312, the transceiver 316, the actuator 330, the support positioning system 360, the medical imaging system 303, and the radiation beam therapy system 301 are shown as all being connected to the hardware interface 106 of the computer system 102.

In this example the computer storage 110 is shown as containing a pulse sequence 370 which contains instructions or data which may be turned into instructions for controlling the magnetic resonance imaging system 302. The pulse sequence 370 may actually be multiple pulse sequences. The computer storage 372 is shown as containing magnetic resonance data 372 which was acquired using the pulse sequence 370. The computer storage 110 is further shown as containing a magnetic resonance image 374 which was reconstructed from the magnetic resonance data 372. The computer storage 110 is further shown as containing thermal magnetic resonance data 376 which is also acquired with a variation of the pulse sequence 370. The computer storage 378 is shown as containing a measured thermal distribution 378 around the target zone 340 and the path of the ultrasound 332. The computer storage is further shown as containing medical image data 380 acquired by the medical imaging system 303 within the imaging zone 318'. The computer storage 110 is further shown as containing a medical image 382 reconstructed from the medical image data 380. The computer storage is shown as containing a predicted thermal distribution 384 and ultrasound control command data 386.

The computer memory 112 is further shown as containing an image reconstruction module 390 which contains instructions which enable the processor 104 to reconstruct the magnetic resonance image 374 from the magnetic resonance data 372, the measured thermal distribution 378 from the thermal magnetic resonance data 376, and the medical image 382 from the medical image data 380. The computer storage is shown as further containing an image registration module 392 which may be used for instance for registering the treatment plan 120 to the magnetic resonance image 374 and/or the medical image 382. The computer memory 112 is further shown as containing a high-intensity focused ultrasound simulation module 394 which is used to generate the predicted thermal distribution 384 and the ultrasound control command data 386 using data contained within the treatment plan 120. The magnetic resonance imaging system 302 and the high-intensity focused ultrasound system 304 may be at a separate location from the radiation beam therapy system 301 and the medical imaging system 303.

The medical apparatus 300 may be used in a variety of ways. For instance the subject may be first placed into the magnetic resonance imaging system 302 to perform sonication using the high-intensity focused ultrasound system 304 and then placed into the radiation beam therapy system 301. Alternatively the subject 320 may first be irradiated with the radiation beam therapy system 301 and then later sonicated using the high-intensity focused ultrasound system 304.

Figure 4:
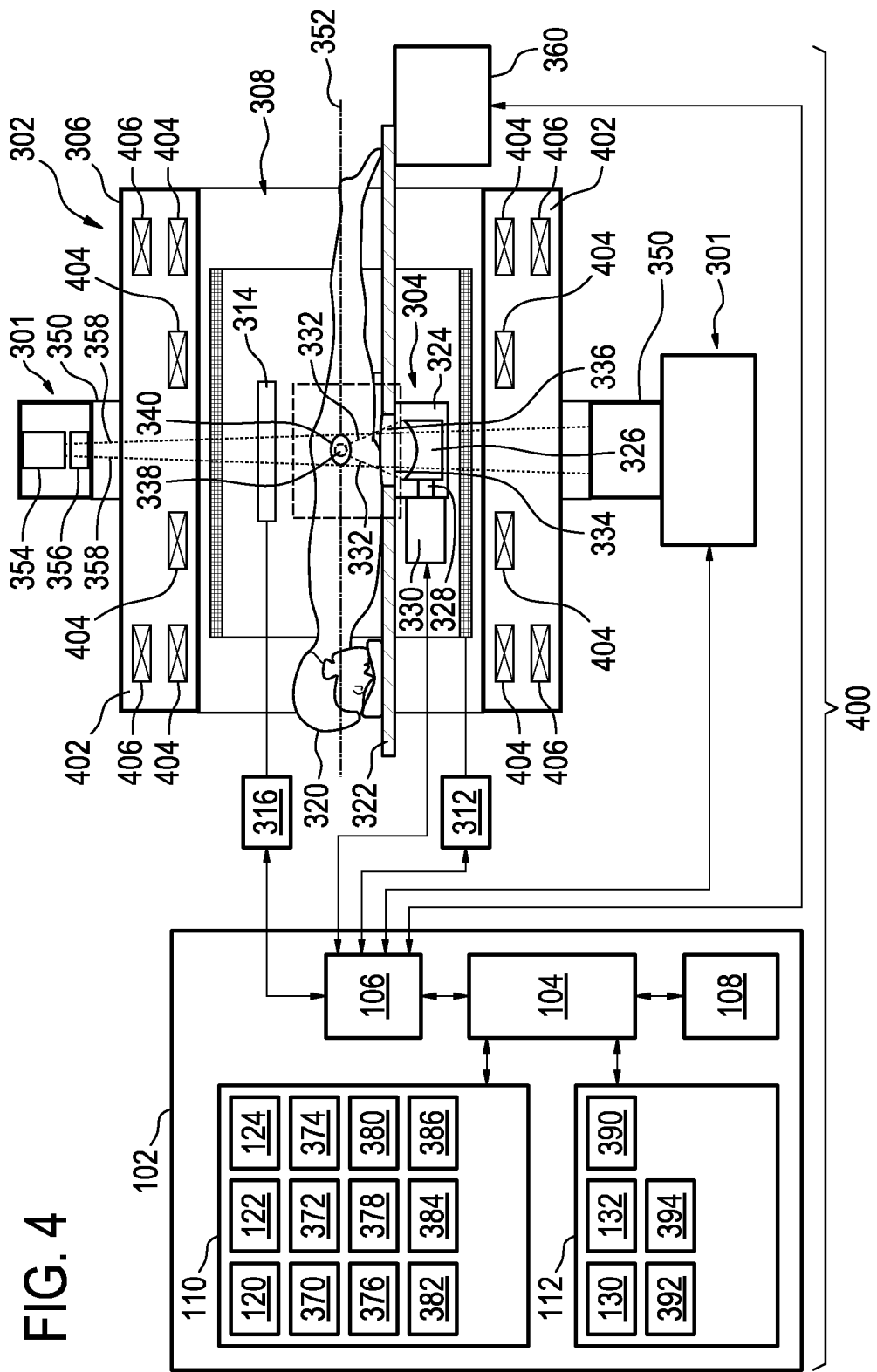
FIG. 4 illustrates a further example of a medical apparatus.

FIG. 4 illustrates a further example of a medical apparatus 400. In this example the radiation beam therapy system 301 has been integrated into the magnetic resonance imaging system 302 and the high-intensity focused ultrasound system 304. The magnetic resonance imaging system 302 fulfills the function of the medical imaging system 303.

The magnet 306 is a superconducting magnet and more details are shown in this Fig. than in FIG. 3. There is a cryostat 402 with several superconducting coils 404. There is also a compensation coil 406 which may be used to create an area of reduced magnetic field which surrounds the magnet 306. The radiation beam therapy system 301 in this embodiment is intended to be representative of radiation therapy systems in general. The components shown here are typical for LINAC and x-ray therapy systems. However with minor modifications such as using a split magnet charged particles or beta particle radiation therapy systems can also be illustrated using this diagram. The walls of the magnet 306 may attenuate the radiation beam 358, however materials can be chosen to minimize this. The superconducting coils 404 and compensation coils can be positioned out of the way of the radiation beam path 358.

In the example shown in FIG. 4 the medical apparatus 400 may be operated in several different ways. For instance the subject may first sonicate with the high-intensity focused ultrasound system 304 and then irradiate the subject 320 using the radiation beam therapy system 301. The medical apparatus 400 may also be operated such that the sonication of the subject 320 is at least partially performed during the irradiation of the subject 320 using the radiation beam therapy system 301. The medical apparatus 400 may also be operated such that the subject 320 is irradiated first using the radiation beam therapy system 301 and then later sonicated using the high-intensity focused ultrasound system 304.

Hyperthermia delivered by High Intensity Focused Ultrasound (HIFU) is a known method to sensitize tissue to locally improved radiotherapy treatment. However HIFU hyperthermia heating pattern tends to sensitize not only targeted tumoral tissue but also surrounding healthy tissue within the HIFU beam path. As consequence excessive collateral damage of this sensitized healthy tissue can occur while using with standard radiotherapy treatment with HIFU hyperthermia. The proposed invention consists to modify the radiotherapy treatment planning to reduce collateral damage by turning off the radiotherapy beams aligned with the ultrasound beam path.

The use of hyperthermia is an efficient way to sensitize tissue to either improve the radiotherapy treatment outcome or to reduce the radiotherapy dose applied. The recent developments of High Intensity Focused Ultrasound (HIFU) technology guided by Magnetic Resonance Imaging (MRI) offers the possibility to precisely control the localisation and the temperature level required for an optimal hyperthermia heating of typically 41° C. for 60 min.

The hyperthermia heating pattern delivered by HIFU remains imperfect due to the inherent propagation of the ultrasound energy from the transducer towards the targeted region. As consequence unwanted heating occurs along the ultrasound beam path which sensitizes not only the tumoral tissue in the targeted region but also healthy tissue in the near field (i.e. between the tumor and the transducer) and the far field (behind the tumor along the ultrasound axis). As consequence skin, subcutaneous fat, muscle and other organs in the ultrasound beam path are also subject to unwanted radiotherapy sensitization. This invention proposed a method to adapt the radiotherapy treatment planning as function of the hyperthermia performed to reduce collateral damage of healthy tissue subject to unwanted radiotherapy sensitization.

Since the HIFU hyperthermia provides an accurate control of the temperature distribution in direction orthogonal to the ultrasound beam path but not along the ultrasound beam path, the proposed solution consists to turn off the radio therapy beam when aligned with the ultrasound beam path.

Figure 5:
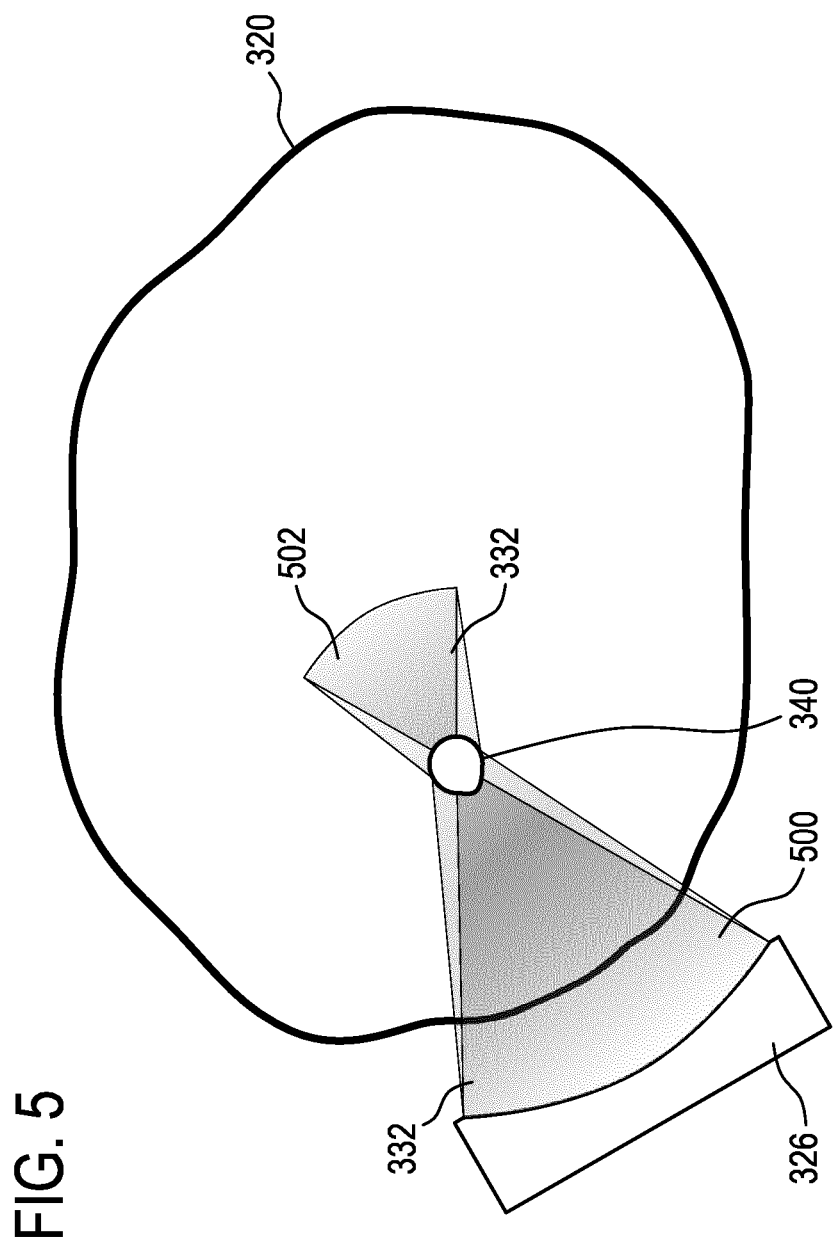
FIG. 5 illustrates the heating of a subject with ultrasound.

FIG. 5 illustrates the heating of the subject 320. The HIFU transducer 326 is aimed at the subject 320 and the ultrasound follows the path 332 into the target zone 340. The path of the ultrasound is made up by a near field 500 and a far field 502. The absorption of ultrasound by the subject is high, so the far field region 502 may in some cases be negligible. The region 332 indicates an ultrasound beam path within the subject.

Figure 6:
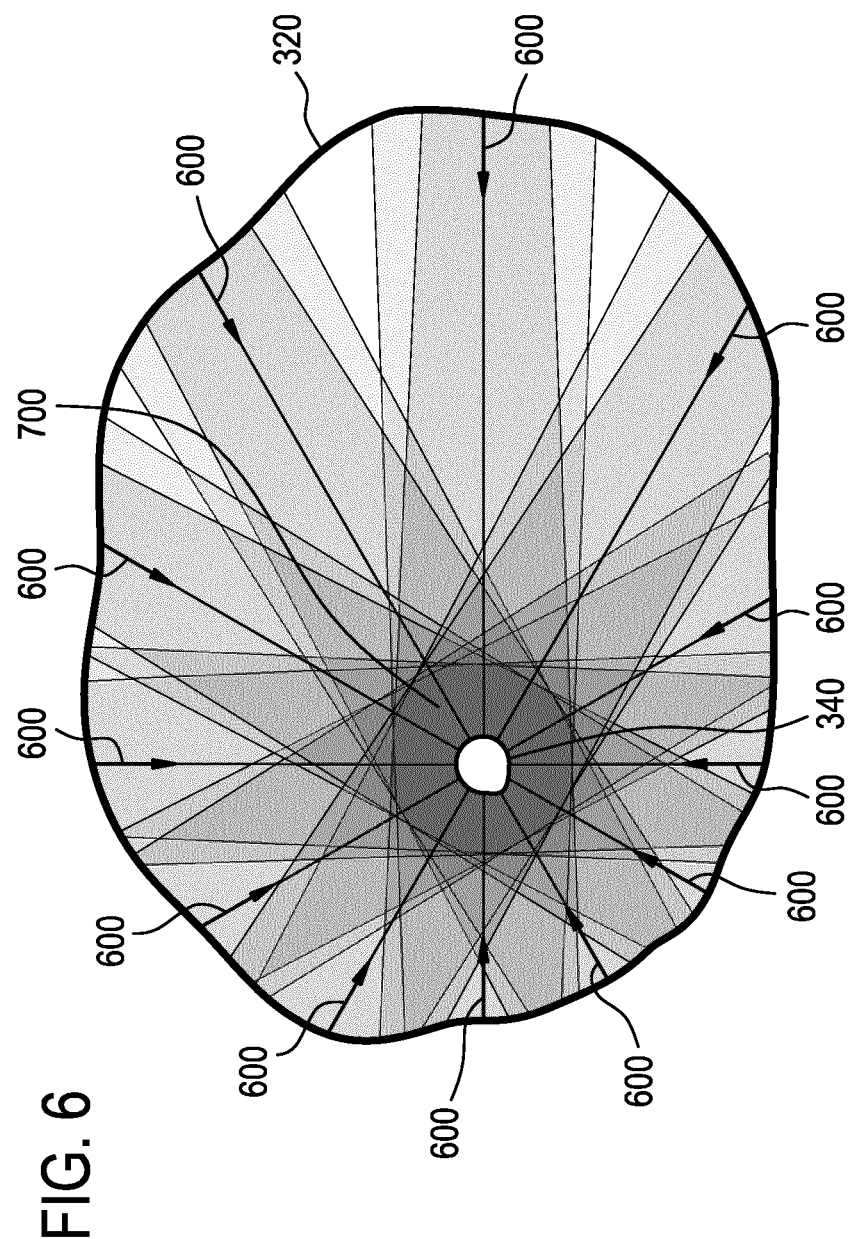
FIG. 6 subject of FIG. 5 being irradiated from several different angles surrounding the subject.

FIG. 6 shows the same subject 320 and target zone 340. The subject 320 has been positioned in a radiation beam therapy system and the radiation source has been rotated to a number of angles to irradiate the target zone 340. The paths indicated by the arrows labeled 600 show different possible paths which the radiation can enter into the subject 320. Comparing FIGS. 5 and 6 it can be seen that a number of the paths will greatly overlap with the ultrasound path 332. This may be undesirable as the regions in area 332 which are not in region 340 of the target zone may suffer from unintentional radiation damage.

The FIGS. 5 and 6 illustrates in an axial view an example of hyperthermia heating pattern (FIG. 5) generated by a focused ultrasound transducer and an example of radiotherapy treatment planning of the same targeted spot (FIG. 6) by applying radiotherapy beams every 30° around the body delineate by a thick solid black line 600.

Figure 7:
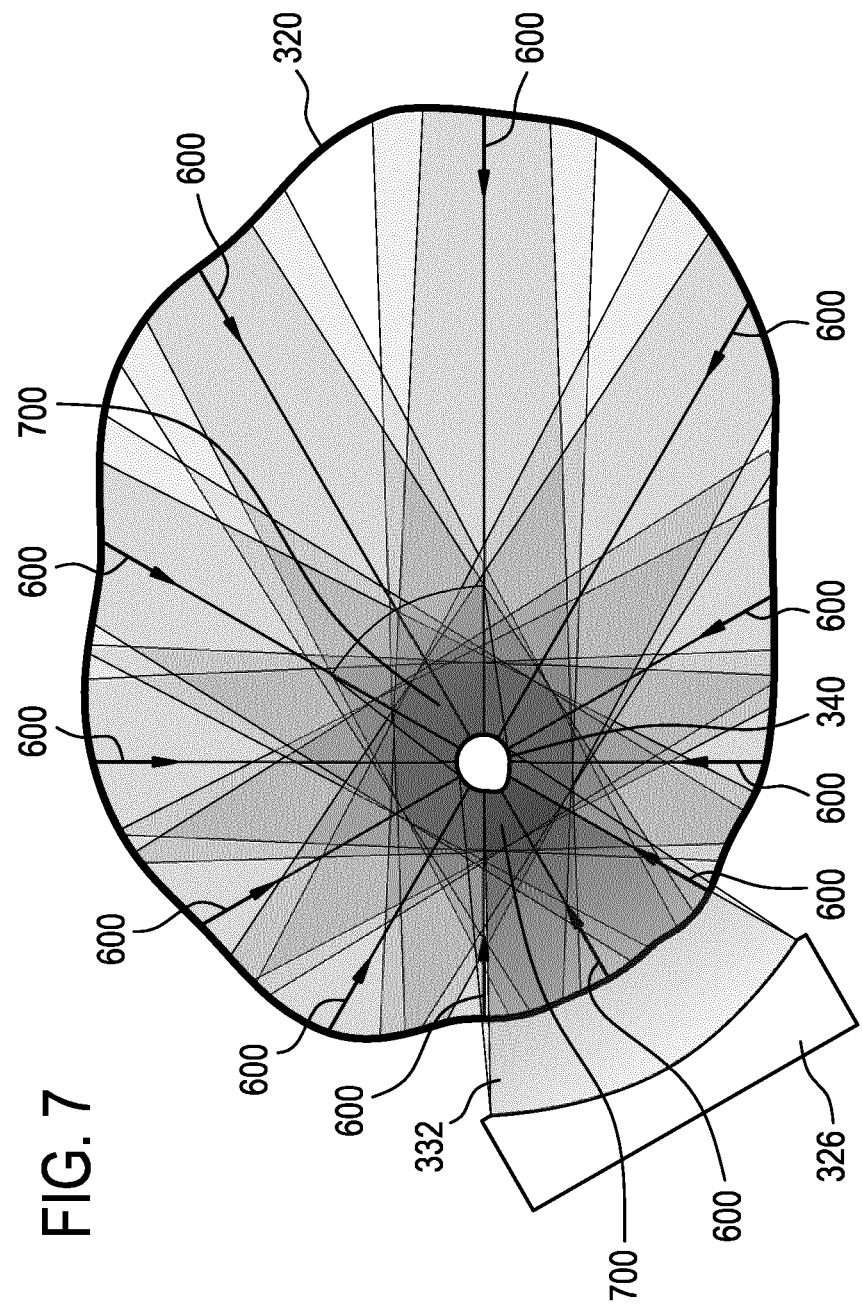
FIG. 7 shows FIGS. 5 and 6 overlapped.

FIG. 7 shows FIGS. 5 and 6 overlapped upon one another. Adjacent to the target zone there can be seen two regions of unintentional radiation damage 700. The region of unintentional radiation damage 700 is where there is a great overlap of radiation beams 600 and the ultrasound 332.

Figure 8:
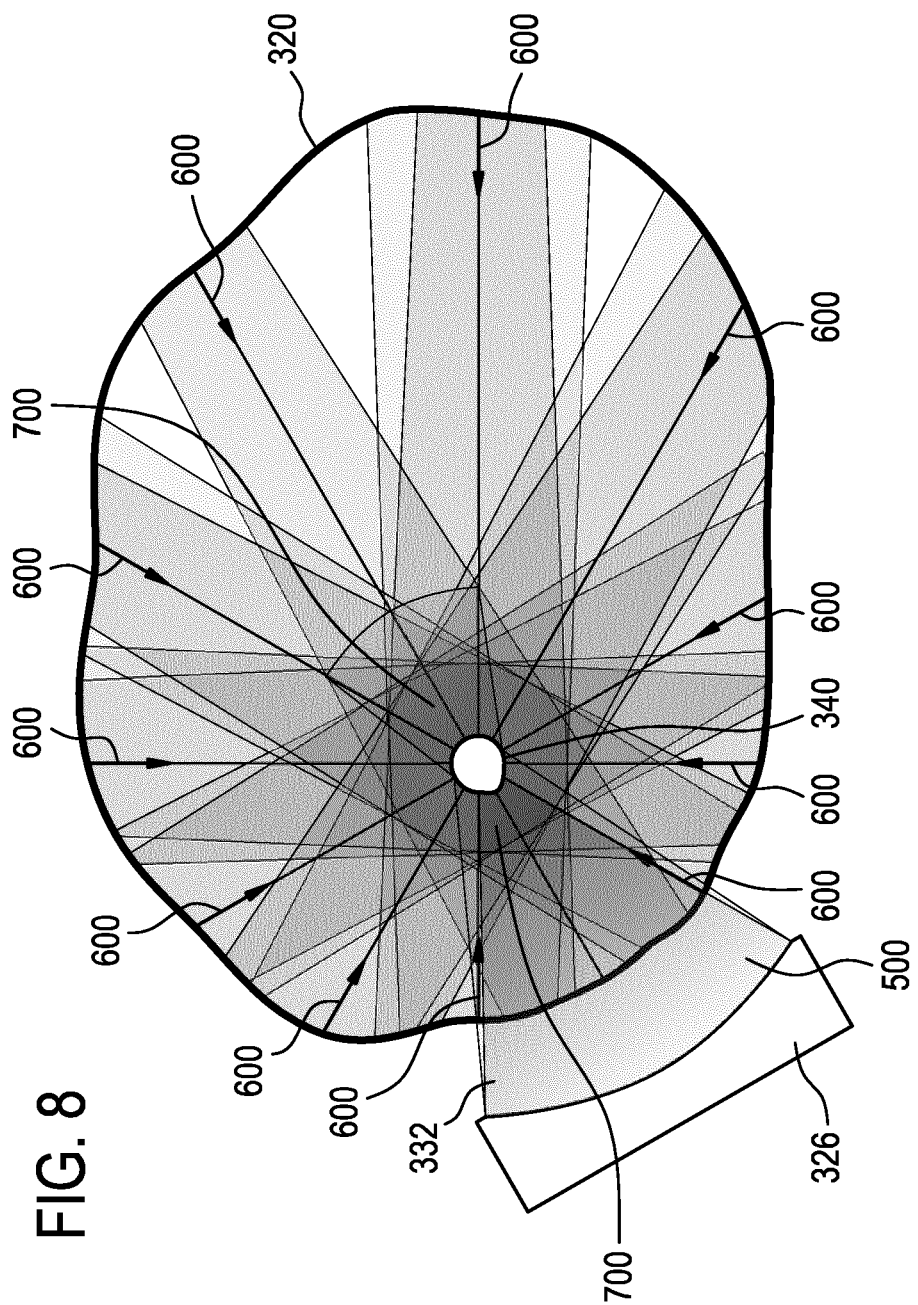
FIG. 8 is similar to that of FIG. 7, however the number of radiation beams has been reduced and the radiation beam is no longer sent in from the near field region of the ultrasound.

FIG. 8 is similar to that of FIG. 7, however the number of radiation beams has been reduced and the radiation beam is no longer sent in from the near field region 500. It can be seen in FIG. 8 that there is less unintentional damage 700 when compared to FIG. 7.

Figure 9:
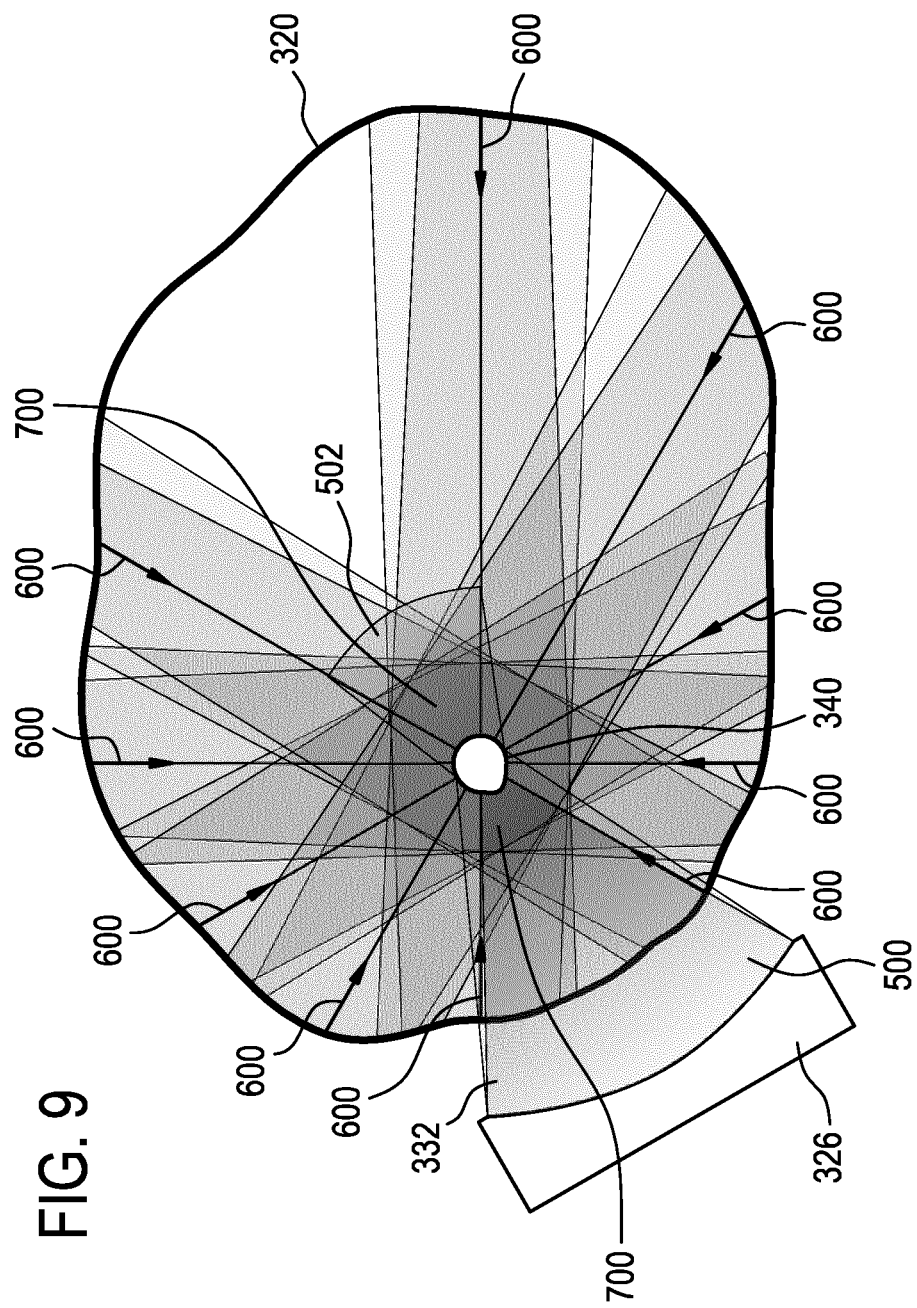
FIG. 9 is also similar to FIG. 7 except the radiation beams going directly into the near field and the far field of the ultrasound have been eliminated.

FIG. 9 is also similar to FIGS. 8 and 7. In FIG. 9 the radiation beams have been further reduced such that the radiation beam directed at the near field 500 and the far field 502 has been eliminated. It can be seen that the area of unintentional damage 700 is smaller than that shown in FIG. 7 or 8.

Figure 10:
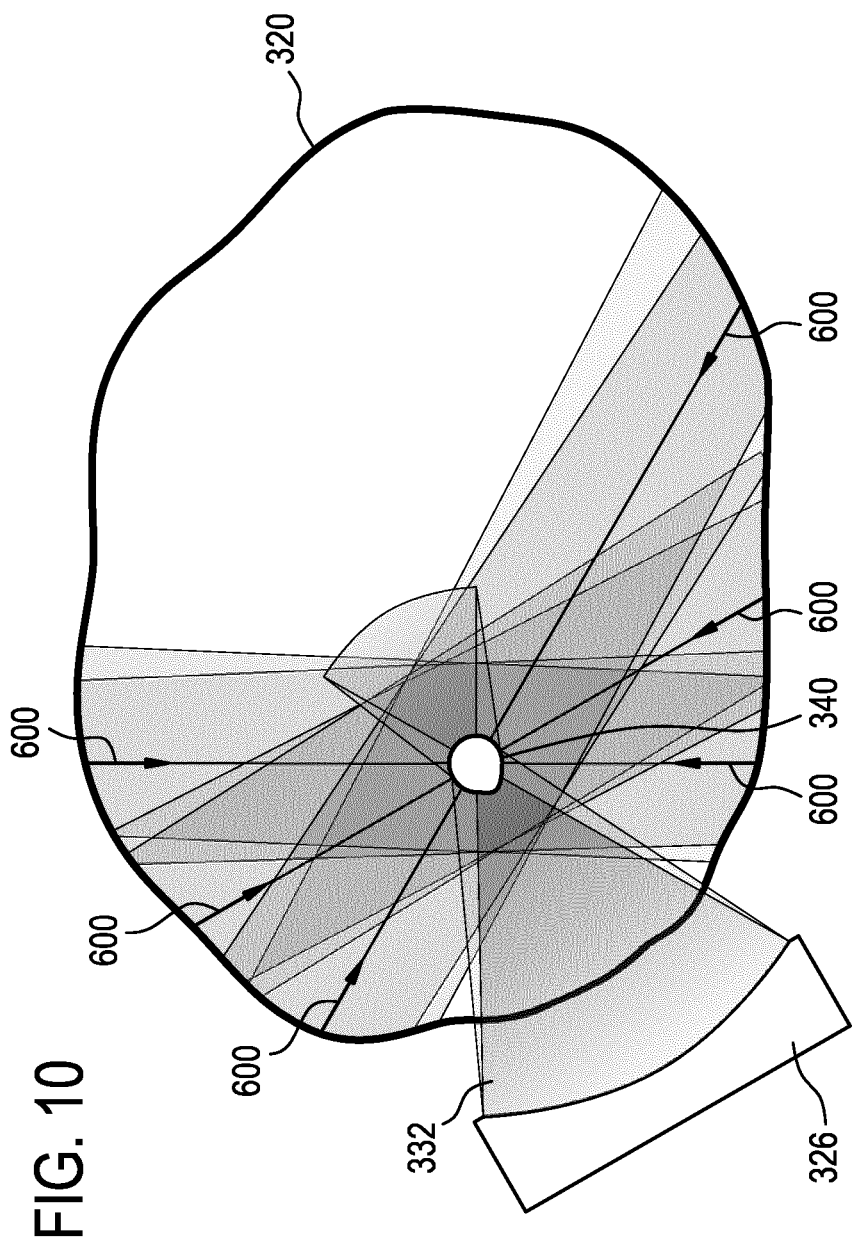
FIG. 10 is similar to the FIG. 7 except the number of radiation beams has been further reduced such that radiation beam paths which intersect the ultrasound beam path by more than a predetermined volume have been eliminated.

FIG. 10 is similar to the Figs. shown in FIGS. 7, 8 and 9. However, in FIG. 10 the number of radiation beams has been further reduced such that radiation beam paths which intersect the ultrasound beam path 322 by more than a predetermined volume have been eliminated. In comparing FIG. 10 to FIGS. 7, 8 and 9 it can be seen that the amount of unintentional damage is greatly reduced. FIG. 10 illustrates the benefit of controlling the radiation beam therapy system such that it does not target the target zone 340 when radiation beam path intersects the ultrasound beam path by more than a predetermined volume. The ultrasound beam path may be defined in terms of a path of the ultrasound above which there is a threshold of vibrational intensity, it may be defined by a thermal dose delivered by the ultrasound, it may also be determined by a region which has a local average temperature divided by time above a predetermined threshold also.

By overlaying the hyperthermia heating pattern with the radiotherapy treatment planning, the FIGS. 7 to 10 describes in a grey scale the tissue damage induced by the combination of hyperthermia with radiotherapy. As shown on FIG. 7, the usage of standard radiotherapy planning with hyperthermia induces excessive damage of tissues in the near and far field of the ultrasound beam path. FIG. 8 shows an alternative radiotherapy treatment planning in which the radio therapy beam coming from the orientation of the ultrasound transducer is turned off to protect healthy near field tissue such as the skin and the subcutaneous fat. In case of vital organs located in the far field of the ultrasound beam path, the radiotherapy beams along both direction of transducer axis can turned off as illustrated in FIG. 9.

For further protection of healthy tissue subject to radio sensitization by hyperthermia, all the radiotherapy beams aligned with a part of the ultrasound beam path can be turned off as presented FIG. 10. It is expected that despite the reduction of the number of radio therapy beam orientations used, a sufficient amount of tissue damage will occur in the target region since the hyperthermia increase significantly the efficacy of the radiotherapy. The resulting modified radiotherapy treatment planning allows compensating for the lack of spatial control of the heating along the transducer beam path.

Focused ultrasound therapeutic transducer has a spherical shape which allows to a form a focal point at the center of this sphere. At this location the ultrasound wave coming from each part of the transducer interferes in constructive way. It creates a small ellipsoidal focal point elongated along the beam axis (or revolution axis of the transducer) defined by the 50% intensity threshold relatively to the maximal intensity at the center. The near-field region is defined as part of the beam path located between the ellipsoidal focal point and the transducer. In opposition, the far field region is defined as part of the beam path located after the focal point away from the transducer.

Figure 11:
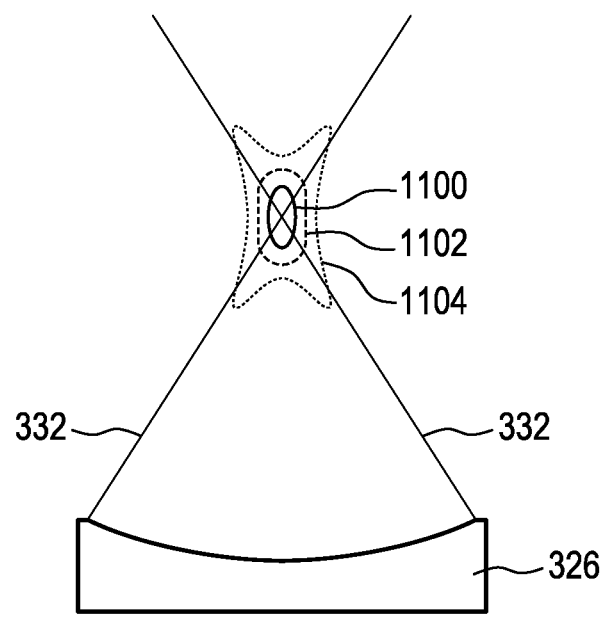
FIG. 11 illustrates the path of ultrasound generated by a transducer.

As illustrated FIG. 11, the curved transducer generates an ultrasound wave mainly contained within the cone beam shape represented by hairlines 332. On this figure the intensity thresholds at 50% 1100, 25% 1102 and 12.5% 1104 are delimited by solid, dash and dot lines respectively. Applying this intensity distribution on a biologic tissue generates a temperature rise which has a similar spatial distribution. On FIG. 1, solid, dash and dot lines can also represent an average heating distribution of 45° C. 1100, 41° C. 1102 and 39° C. 1104 respectively while performing sonication in a single point sonication inside biologic tissue initially at 37° C.

FIG. 11 illustrates the path of ultrasound 332 generated by a transducer 326 and illustrates the intensity or the thermal threshold for a single focal point 1100. Since the focal point has a size very close to the ultrasound wave length (i.e., close to 1 mm while using 1.5 MHz in biological tissue with celerity of 1540 m/s) this small focal point is moved to different location in order to perform heating of a large tumoral volume ranging from 1 to 10 cm diameter. As illustrated FIG. 12 and FIG. 13, the focal point can be either moved using electronic steering of the beam path (when using phase array transducer) or by mechanical displacement of the transducer (when using a motorized arm). Because the electronic steering is fast but allows small displacement and mechanical displacement is slow but allows large displacement, to perform hyperthermia of a large region a combination both mechanical and electronic displacements of the focal point are used to cover a large region rapidly.

Figure 12:
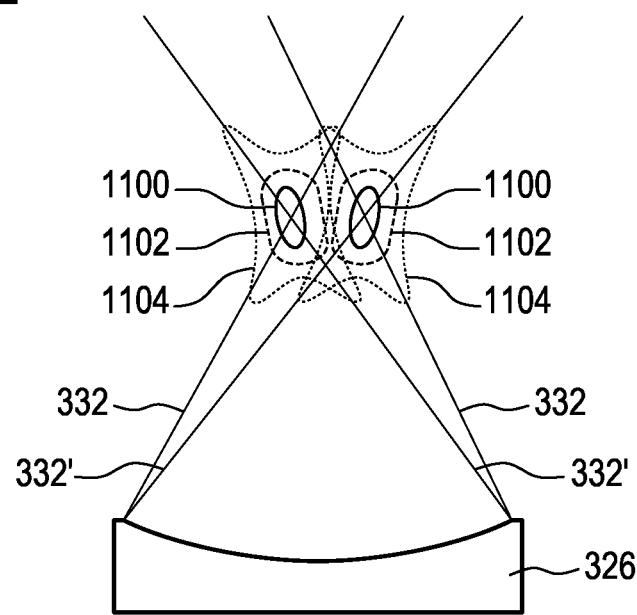
FIG. 12 illustrates the effect of electronic steering of ultrasound.

FIG. 12 illustrates the electronic steering of ultrasound. The path 332 is a first position and the paths labeled 332' indicate ultrasound of a second path controlled using electronic steering.

Figure 13:
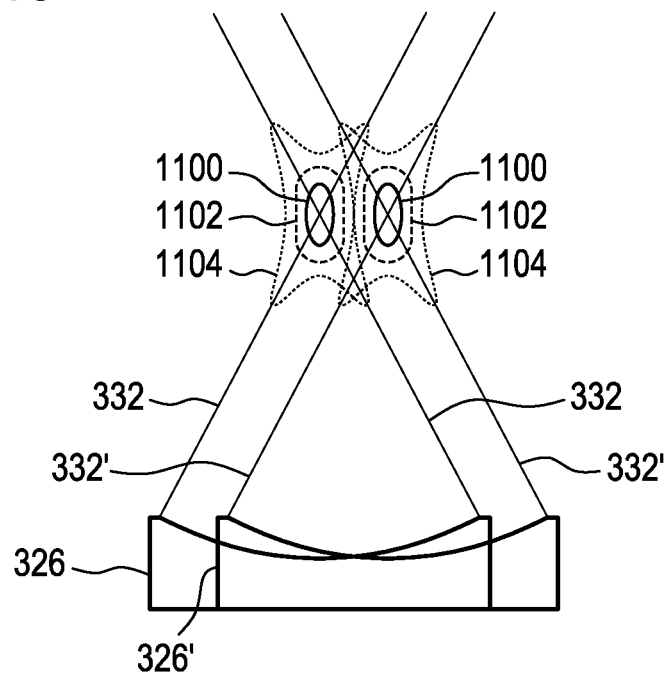
FIG. 13 illustrates the effect of the mechanical displacement of an ultrasound transducer.

FIG. 13 illustrates mechanical displacement of the transducer 326. The transducer is shown in a first position 326 and a second position 326'. In the first position 326 the ultrasound follows the path 332. In the second position 326' the ultrasound follows the path 332'.

Figure 14:
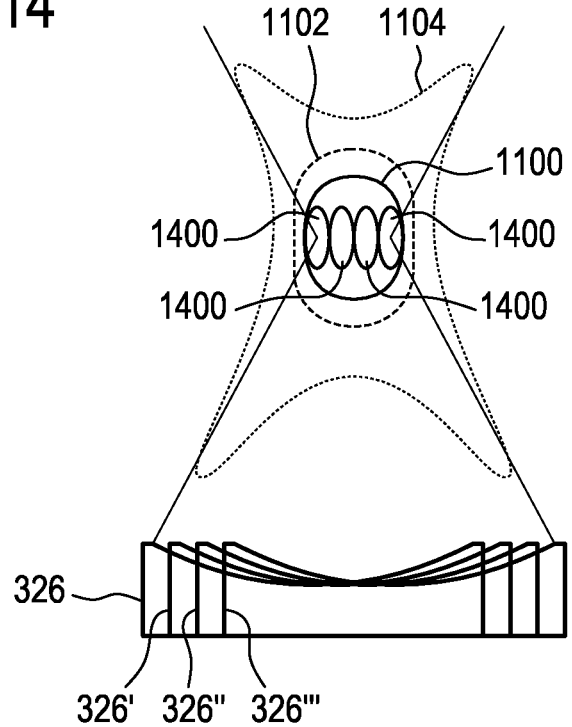
FIG. 14 illustrates the average thermal threshold or average thermal dose threshold using several sonication points.

FIG. 14 shows the transducer in four different positions 326, 326', 326", 326"'. FIG. 14 illustrates the average thermal threshold or average thermal dose threshold using several sonication points. The sonication points are labeled 1400.

While using a large number of focal points 1400 to cover a large region, the heating induce by each focal point add to each other not only within the focal point region but also along all beam paths. The FIG. 14 illustrates an example of 4 focal points located next to each other. The resulting average heating distribution at 45° C. 1100, 41° C. 1102 and 39° C. 1104 are represented with solid, dash and dot lines respectively. The usage of a large number of focal point position increases the size of the heated zone in the near field as well as the far field.

FIG. 14 illustrates the intensity or the average thermal threshold or the thermal dose threshold using multiple sonication points.

The heating distribution can be characterized using the average heating per unit of time to assess the radio-sensitization gain. Alternatively the effect of the hyperthermia on cell damage (and thus radio the radio-sensitization gain) can be evaluated using the thermal dose concept as defined by Sapareto and Dewey in 1984. The thermal dose in EM43 is defined as the heating time equivalent to an heating at 43° C. using the integration of the temperature as defined in this equation:

$$t_{43} = \int_0^t R^{43-T(t)} dt \; avec \; \begin{cases} R = 0.25 \; si \; T < 43° \text{ C.} \\ R = 0.5 \; si \; T \geq 43° \text{ C.} \end{cases}$$

As consequence if the heating pattern described FIG. 14 would be maintained for 30 minutes with the thresholds of 45° C., 41° C. and 39° C. defined by the solid, dash and dot lines respectively, the same lines would also represents a thermal dose thresholds of 120 EM43, 2 EM43 and 0.1 EM43.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 medical apparatus
102 computer
104 processor
106 hardware interface
108 user interface
110 computer storage
112 computer memory 120 treatment plan
122 planning thermal distribution
124 radiation control command data
130 control module
132 radiation control command generation module
300 medical apparatus
301 radiation beam therapy system
302 magnetic resonance imaging system
303 medical imaging system
304 high intensity focused ultrasound system
306 magnet
308 bore of magnet
310 magnetic field gradient coil
312 magnetic field gradient coil power supply
314 radio frequency coil
316 transceiver
318 imaging zone
318' imaging zone
320 subject
322 subject support
324 fluid filled chamber
326 ultrasonic transducer
328 mechanical positioning system
330 actuator
332 path of ultrasound
334 ultrasound window
336 gel pad
338 sonication point
340 target zone
350 gantry
352 axis of rotation
354 radiation source
356 collimator
358 radiation beam
360 support positioning system
370 pulse sequence
372 magnetic resonance data
374 magnetic resonance image
376 thermal magnetic resonance data
378 measured thermal distribution
380 medical image data
382 medical image
384 predicted thermal distribution
386 ultrasound control command data
390 image reconstruction module
392 image registration module
394 high intensity focused ultrasound simulation module
400 medical apparatus
402 cryostat
404 superconducting coil
406 compensation coil
500 near field
502 far field
600 radiation beam path
1100 intensity threshold 50%
1102 intensity threshold 25%
1104 intensity threshold 12.5%
1400 sonication point

The invention claimed is:

1. A medical apparatus comprising:
a processor for controlling the medical apparatus,
a memory containing machine executable instructions for execution by the processor, wherein execution of the machine executable instructions causes the processor to:
receive a treatment plan descriptive of an ionizing radiation beam treatment of a target zone within a subject using a radiation beam therapy system, wherein the radiation beam therapy system comprises a radiation source and a gantry for rotating the radiation source about a rotational axis, wherein the radiation source is operable for irradiating a radiation beam path, wherein the radiation source is operable for aiming the radiation beam path at the rotational axis;
receive a planning thermal distribution descriptive of ultrasound heating of the subject with a high intensity focused ultrasound system wherein the planning thermal distribution is spatially dependent, wherein the planning thermal distribution is descriptive of a heating zone and an ultrasound beam path within the subject, wherein the target zone is within the heating zone; and
generate radiation control command data for controlling the radiation beam therapy system to irradiate the target zone using the planning thermal distribution and the treatment plan, wherein the radiation control command data is executable to cause the radiation source to reduce irradiation of the target zone when more than a predetermined volume of the radiation beam path intersects the ultrasound beam path.

2. The medical apparatus of claim 1, wherein execution of the instructions further cause the processor to calculate a predicted thermal distribution and ultrasound control command data using the treatment plan and a high intensity focused ultrasound simulation model, wherein the ultrasound control command data is executable for controlling the high intensity focused ultrasound system to cause the high intensity focused ultrasound system to heat the subject according to the predicted thermal distribution, wherein the high intensity focused ultrasound simulation model is descriptive of the high intensity focused ultrasound system.

3. The medical apparatus of claim 2, wherein the planning thermal distribution is the predicted thermal distribution, wherein execution of the instructions further cause the processor to first control the radiation beam therapy system to execute radiation therapy control commands and second control the high intensity focused ultrasound system to execute the ultrasound control command data.

4. The medical apparatus of claim 2, wherein execution of the instructions further cause the processor to control the radiation beam therapy system to execute radiation therapy control commands and control the high intensity focused ultrasound system to execute the ultrasound control command data simultaneously.

5. The medical apparatus of claim 4, wherein execution of the instructions further cause the processor to acquire thermal magnetic resonance data descriptive of the heating zone and the ultrasound beam path using a magnetic resonance imaging system during the execution of the ultrasound control command data, wherein execution of the instructions further cause the processor to calculate a measured thermal distribution using the thermal magnetic resonance data, wherein execution of the instructions further cause the processor to modify the radiation control command data using the treatment plan and the measured thermal distribution.

6. The medical apparatus of claim 2, wherein the planning thermal distribution is a measured thermal distribution, wherein execution of the instructions further cause the processor to first control the high intensity focused ultrasound system to execute the ultrasound control command data and second control radiation beam therapy system to execute the radiation therapy control commands, wherein execution of the instructions further cause the processor to acquire thermal magnetic resonance data descriptive of the heating zone and the ultrasound beam path using a magnetic resonance imaging system during the execution of the ultrasound control command data, wherein execution of the instructions further cause the processor to calculate the measured thermal distribution using the thermal magnetic resonance data.

7. The medical apparatus of claim 1, wherein the medical apparatus further comprises the high intensity focused ultrasound system.

8. The medical apparatus of claim 1, wherein the medical apparatus further comprises the radiation beam therapy system.

9. The medical apparatus of claim 1, wherein the medical apparatus further comprises the radiation beam therapy system, wherein the radiation beam therapy system further comprises the high intensity focused ultrasound system, and wherein the radiation beam therapy system further comprises a magnetic resonance imaging system.

10. The medical apparatus of claim 1, wherein the radiation beam therapy system is any one of the following: a LINAC system, a charged particle therapy system, an X-ray system, and a gamma radiation beam therapy system.

11. The medical apparatus of claim 1, wherein the planning thermal distribution is descriptive of a local average temperature divided by time.

12. The medical apparatus of claim 1, wherein the planning thermal distribution is a thermal dose.

13. A computer program product comprising: a non-transitory computer readable storage medium having machine executable instructions stored thereon for execution by a processor controlling a medical apparatus, wherein the medical apparatus comprises the processor and execution of the machine executable instructions causes the processor to:
  receive a treatment plan descriptive of an ionizing radiation beam treatment of a target zone within a subject using a radiation beam therapy system, wherein the radiation beam therapy system comprises a radiation source and a gantry for rotating the radiation source about a rotational axis, wherein the radiation source is operable for irradiating a radiation beam path, wherein the radiation source is operable for aiming the radiation beam path at the rotational axis;
  receive a planning thermal distribution descriptive of ultrasound heating of the subject with a high intensity focused ultrasound system, wherein the planning thermal distribution is spatially dependent, wherein the planning thermal distribution is descriptive of a heating zone and an ultrasound beam path within the subject, wherein the target zone is within the heating zone; and
  generate radiation control command data for controlling the radiation beam therapy system to irradiate the target zone using the planning thermal distribution and the treatment plan, wherein the radiation control command data is executable to cause the radiation source to reduce irradiation of the target zone when more than a predetermined volume of the radiation beam path intersects the ultrasound beam path.

14. A method of operating a medical apparatus, wherein the method comprises the steps of:
  receiving a treatment plan descriptive of an ionizing radiation beam treatment of a target zone within a subject using a radiation beam therapy system, wherein the radiation beam therapy system comprises a radiation source and a gantry for rotating the radiation source about a rotational axis, wherein the radiation source is operable for irradiating a radiation beam path, wherein the radiation source is operable for aiming the radiation beam path at the rotational axis;
  receiving a planning thermal distribution descriptive of ultrasound heating of the subject with a high intensity focused ultrasound system, wherein the planning thermal distribution is spatially dependent, wherein the planning thermal distribution is descriptive of a heating zone and an ultrasound beam path within the subject, wherein the target zone is within the heating zone; and
  generating radiation control command data for controlling the radiation beam therapy system to irradiate the target zone using the planning thermal distribution and the treatment plan, wherein the radiation control command data is executable to cause the radiation source to reduce irradiation of the target zone when more than a predetermined volume of the radiation beam path intersects the ultrasound beam path.

15. A method of radiation therapy comprising the steps of:
  receiving a treatment plan, wherein the treatment plan is descriptive of an ionizing radiation beam treatment of a target zone within a subject using a radiation beam therapy system, wherein the radiation beam therapy system comprises a radiation source and a gantry for rotating the radiation source about a rotational axis, wherein the radiation source is operable for irradiating a radiation beam path, wherein the radiation source is operable for aiming the radiation beam path at the rotational axis;
  placing a subject into a high intensity focused ultrasound system, wherein the high intensity focused ultrasound system comprises a magnetic resonance imaging system;
  acquiring image magnetic resonance data using the magnetic resonance imaging system;
  reconstruct a magnetic resonance image using the image magnetic resonance data;
  generating ultrasound control command data for controlling the high intensity focused ultrasound system using a high intensity focused ultrasound simulation model, the treatment plan, and the magnetic resonance image, wherein the high intensity focused ultrasound simulation model is descriptive of the high intensity focused ultrasound system;
  sonicating the subject by executing the ultrasound control command data;
  measuring thermal magnetic resonance data during the sonication of the subject;
  calculating a measured thermal distribution using the thermal magnetic resonance data;
  placing the subject into the radiation therapy beam system, wherein the radiation beam therapy system comprises a medical imaging system for acquiring medical image data;
  generating radiation control command data for controlling the radiation beam therapy system to irradiate the target zone using the measured thermal distribution, the treatment plan, and the medical image data, wherein the radiation control command data is executable to cause the radiation source to reduce irradiation of the target zone when more than a predetermined volume of the radiation beam path intersects an ultrasound beam path; and irradiating the subject by executing the radiation control command data.

\* \* \* \* \*